United States Patent [19]

Kondo

[11] Patent Number: 5,779,626
[45] Date of Patent: Jul. 14, 1998

[54] ENDOSCOPE

[75] Inventor: Mituo Kondo, Omiya, Japan

[73] Assignee: Fuji Photo Optical Co., Ltd., Omiya, Japan

[21] Appl. No.: 723,876

[22] Filed: Sep. 23, 1996

[30] Foreign Application Priority Data

Sep. 29, 1995 [JP] Japan ................................. 7-252265

[51] Int. Cl.⁶ ...................................................... A61B 1/04
[52] U.S. Cl. ............................ 600/130; 600/139; 600/150
[58] Field of Search .................................. 600/130, 139, 600/150, 153, 156, 161

[56] References Cited

U.S. PATENT DOCUMENTS 4,911,147  3/1990  Washizuka ........................ 600/161
5,257,618  11/1993  Kondo ............................. 600/150

*Primary Examiner*—Beverly M. Flanagan
*Attorney, Agent, or Firm*—Sixbey, Friedman, Leedom & Ferguson; David S. Safran

[57] ABSTRACT

Plural contents such as a light guide and a forceps tube, which are inserted into an insertion part of an endoscope, are connected with each other via an elastic member such as thin wall tubes, etc. at one or more positions in the insertion part. The elastic member changes its form with the dislocation of the contents in the longitudinal direction of the insertion part resulting from the bending of the insertion part. If the insertion part is straightened, the contents are restored to their original positions by the restitutive force of the elastic member.

7 Claims, 4 Drawing Sheets

ENDOSCOPE

BACKGROUND OF THE INVENTION

1. Field of the Invention

The present invention relates to an endoscope, and more particularly to an endoscope which improves the durability of the contents inserted into an insertion part of the endoscope.

2. Description of the Related Art

As shown in FIG. 5, an ordinary endoscope has an operating part 10, which is held by hand, and the operating part 10 connects to an insertion part 12. A bending part 14 is formed at the tip of the insertion part 12, and it is operated and bent remotely by the rotation of an operating knob 18 provided in the operating part 10. Incidentally, a tip hard part 16 is provided at the tip of the bending part 14, and an objective lens, an illumination lens, a forceps channel, an air/water supply opening, etc. (not shown) are provided in the tip hard part 16.

FIG. 6 is a sectional view taken along line 6—6 in FIG. 5. As shown in the figure, a plurality of contents such as light guides 20 and 20, which transmit illumination light to the illumination lens in the tip hard part 16, a forceps tube 22, an image guide 24, which transmits an observed image formed by the objective lens in the tip hard part 16, and so forth are loosely inserted into the insertion part 12. Incidentally, the reference numbers 26 indicate angle wires for operating the bending part 14. An air/water supply tube, etc. (not shown in FIG. 6) are also loosely inserted into the insertion part 12. The endoscope in FIG. 5 is a fiber scope, but in the case of an electronic scope, a signal cable, which connects to a solid state imaging device (e.g. a charge coupled device) provided in the tip hard part 16, is provided instead of the image guide 24. In the case of an ultrasonic scope, a signal cable, which connects to an ultrasonic probe provided in the tip hard part 16, is provided instead of the image guide 24.

The insertion part 12 of the endoscope is inserted into a body and bent in a variety of forms, so that the contents inserted into the insertion part 12 can move freely in the direction of the diameter of the insertion part 12 as shown with arrows in FIG. 6, and in the longitudinal direction of the insertion part 12. Incidentally, because the contents move freely in the insertion part 12, the contents do not disturb the movement of the insertion part 12.

However, if the contents move within the insertion part of the endoscope, some contents with weak restitutive force cannot return to their original positions in the insertion part; as a result, the contents develop kinks, or the like, and there are problems in that the light guide, the image guide, and the signal cable are broken, and the tube is crushed, and the like.

SUMMARY OF THE INVENTION

The present invention has been developed under the above-described circumstances, and has its object the provision of an endoscope which ensures that the contents inserted into an insertion part of the endoscope move freely, and restores the contents to their original positions if they move, so as to improve the durability of the contents.

In order to achieve the aforementioned object, in the present invention, plural contents loosely inserted into the insertion part of the endoscope are connected with each other via an elastic member at one or more positions in the insertion part; and the elastic member changes its form with dislocation of the contents in the longitudinal direction of the insertion part resulting from bending of the insertion part, and restores the contents to their original positions by the restitutive force thereof if the insertion part is straightened. For example, even if the dislocation occurs in the contents in the longitudinal direction of the insertion part, some contents return to their original positions easily (they have strong restitutive force) when the cause of the dislocation is eliminated. The other contents do not easily return to their original positions (they have weak restitutive force). These contents of two types are connected with each other via an elastic member, so that the contents with the weak restitutive force can return to their original positions.

Elastic thin wall tubes of a predetermined length are employed as the elastic member. Each of the thin wall tubes covers each of the contents and is adhered to the content at both ends thereof, and the thin wall tubes covering the contents are adhered to each other at the central part thereof.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein.

DETAILED DESCRIPTION OF THE PREFERRED EMBODIMENTS

Figure 1:
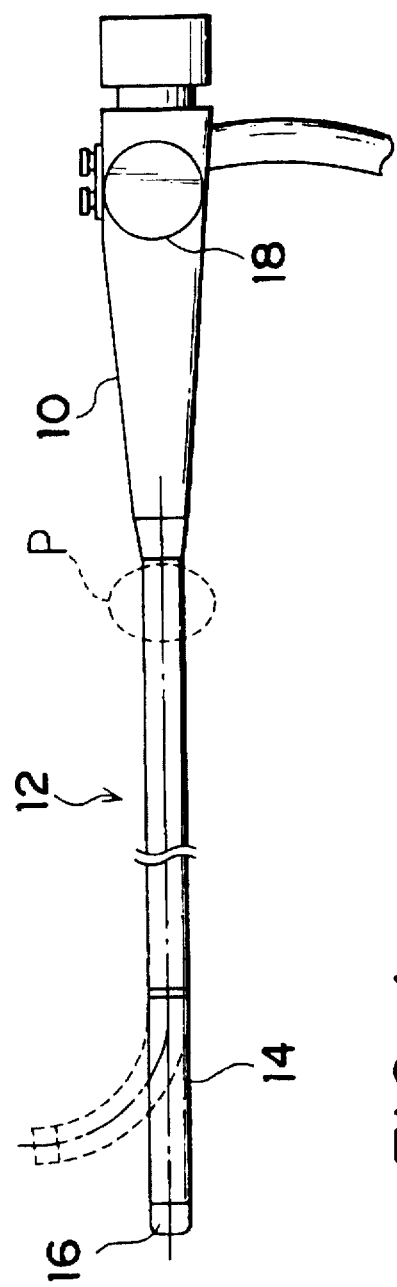
FIG. 1 is a view illustrating the appearance of an endoscope according to the present invention.
Figure 5:
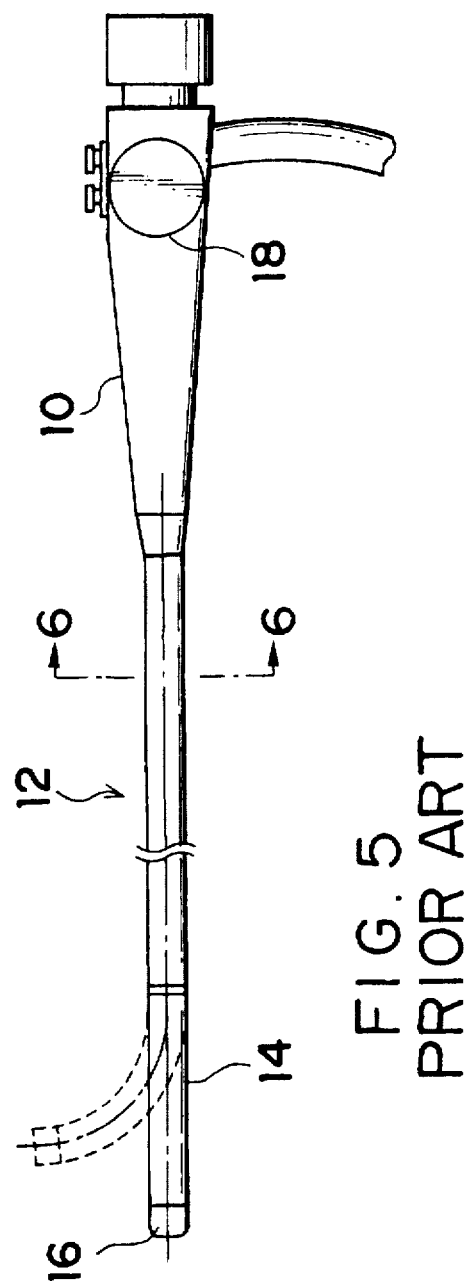
FIG. 5 is a view illustrating the appearance of the conventional endoscope.
Figure 6:
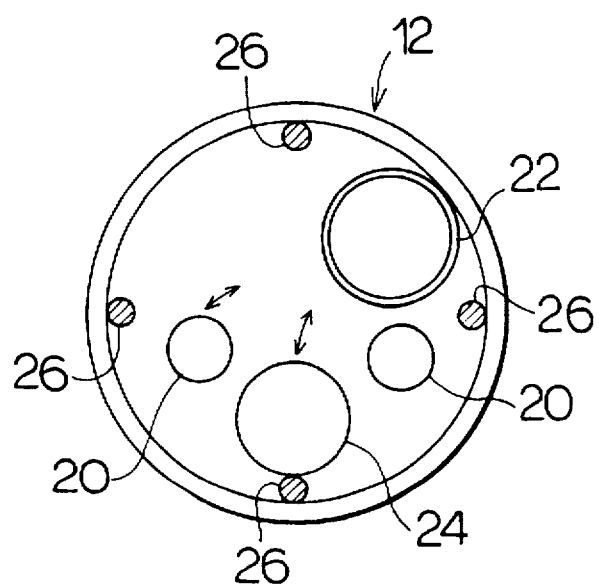
FIG. 6 is a sectional view taken along line 6-6 in FIG. 5.

FIG. 1 is a view illustrating the appearance of an endoscope according to the present invention. Parts similar to those in FIGS. 5 and 6 are denoted by the same reference numerals, and they will not be explained.

Figure 2:
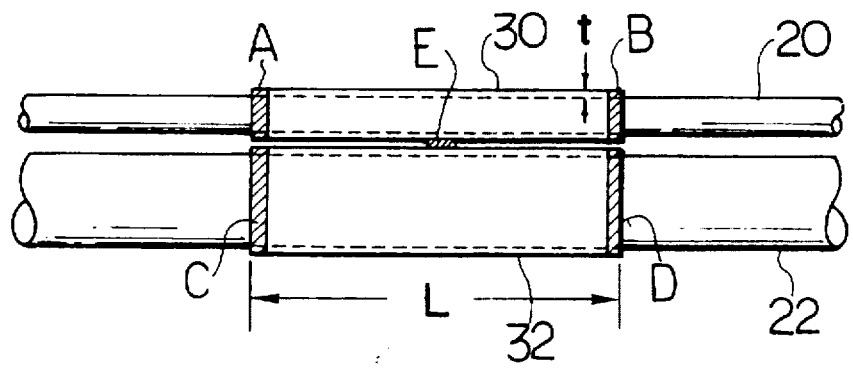
FIG. 2 is a view illustrating an example in which a light guide connects with a forceps tube via thin wall tubes.

In this embodiment, the contents are connected with each other via an elastic member at a position P in FIG. 1 at the insertion part 12 of the endoscope. FIG. 2 is a view showing an example in which the light guide 20 connects with the forceps tube 22 at the position P.

As shown in FIG. 2, thin wall tubes 30 and 32 are employed as an elastic member, which elastically connects the light guide 20 and the forceps tube 22. The thin wall tubes 30 and 32 have a length (L) of 20–50 mm and a thickness (t) of 0.1 mm for example, and they are made of silicone rubber.

The thin wall tube 30 covers the light guide 20, and it is adhered to the light guide 20 at both ends thereof A and B with an adhesive made from rubber. Likewise, the thin wall tube 32 covers the forceps tube 22, and it is adhered to the forceps tube 22 at both ends thereof C and D. The thin wall tubes 30 and 32 are adhered to each other at a position E at the center of the tube.

Next, an explanation will be given about the operation of the endoscope according to the present invention.

Figure 3:
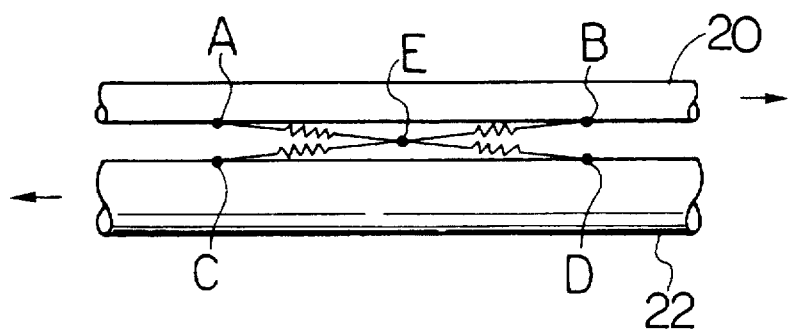
FIG. 3 is a notional view of FIG. 2 illustrating the thin wall tubes.
Figure 4:
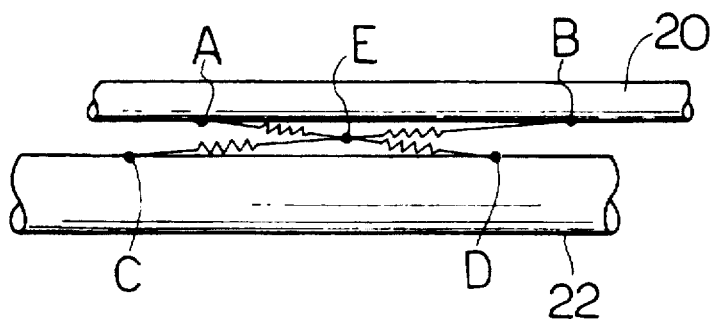
FIG. 4 is a notional view illustrating such a state that the light guide and the forceps tube are dislocated from the positions shown in FIG. 3.

FIG. 3 is a notional view of FIG. 2 showing the thin wall tubes 30 and 32. If the insertion part 12 of the endoscope is bent from the state shown in FIG. 3, the compressive force is applied to the contents located to the inside of a neutral axis of the insertion part 12, and the tensile force is applied to the contents located to the outside of the neutral axis of the insertion part 12. As a result, for example, if the force is applied to the light guide 20 and the forceps tube 22 in the reverse directions as shown with arrows in FIG. 3, the light guide 20 and the forceps tube 22 move in the reverse directions as shown in FIG. 4, so that the dislocation occurs in them. Incidentally, even if the light guide 20 and the forceps tube 22 move in the same direction, the dislocation occurs in them if there is a difference in the movement length between them.

If the dislocation occurs in the light guide 20 and the forceps tube 22 as stated above, the thin wall tubes 30 and 32 expand and contract. That is, as shown in FIG. 4, the thin wall tubes 30 and 32 contract between A and E and between E and D, and expand between B and E and between E and C.

If the insertion part 12 of the endoscope is straightened, the light guide 20 and the forceps tube 22 return to the positions shown in FIG. 3 by the restitutive force of the thin wall tubes 30 and 32. The restitutive force of the forceps tube 22 (the force by which the forceps tube 22 returns to its original position in the insertion part 12) is strong, and the restitutive force of the light guide 20 is weak. When the forceps tube 22 returns to its original position in the insertion part 12, the light guide 20, which is connected with the forceps tube 22 via the thin wall tubes 30 and 32, returns to its original position, too.

Incidentally, in this embodiment, the thin wall tubes are employed as the elastic member for connecting the contents elastically. However, the present invention is not restricted to this. Other elastic members may be used if they can achieve the same effects as the thin wall tubes. A position where the contents are connected with each other via the elastic member is not restricted to the position P in FIG. 1. Moreover, they may be connected at plural positions.

As set forth hereinabove, according to the present invention, the contents, which are inserted into the insertion part of the endoscope, are connected with each other via the elastic member, so that the contents can move freely and the contents return to their original positions without fail by the restitutive force of the elastic member. As a result, the present invention can solve such a problem that the contents are damaged (e.g. the breaking of the light guide, the image guide, the signal cable, etc. and the crash of the tube, and the like) because the contents develop kinks, or the like, so that the durability of the contents can be improved.

It should be understood, however, that there is no intention to limit the invention to the specific forms disclosed, but on the contrary, the invention is to cover all modifications, alternate constructions and equivalents falling within the spirit and scope of the invention as expressed in the appended claims.

I claim:

1. An endoscope wherein:

a forceps tube and other contents are loosely inserted into an insertion part of said endoscope and are connected with each other via an elastic member in said insertion part;

said forceps tube has a first connecting position and a second connecting position which is at a predetermined distance from said first connecting position in a longitudinal direction of said endoscope in order to secure longitudinal expansion of said elastic member;

said other contents have a third connecting position opposite to said first connecting position and a fourth connecting position opposite to said second connecting position; and said elastic member connects said first connecting position to said fourth connecting position, and connects said second connecting position to said third connecting position, said elastic member changing form in the longitudinal direction with dislocation of said forceps tube and other contents as a result of bending of said insertion part, said elastic member restoring said forceps tube and other contents to their original positions by restituitive tensile forces thereof upon elimination of the cause of said bending.

2. The endoscope according to claim 1, wherein said plural contents are two or more of a light guide for transmitting illumination light to an illumination lens at the tip of the endoscope, an image guide for transmitting an observed image formed by an objective lens at the tip of the endoscope, a forceps tube, and an air/water supply tube.

3. The endoscope according to claim 1, wherein said plural contents are two or more of a light guide for transmitting illumination light to an illumination lens at the tip of the endoscope, a signal cable for transmitting an observed image formed on the light accepting surface of a solid state imaging device by an objective lens at the tip of the endoscope, a forceps tube, and an air/water supply tube.

4. The endoscope according to claim 1, wherein said elastic member is elastic thin wall tubes of a predetermined length, each of said thin wall tubes covering each of said contents and being adhered to said content at both ends thereof, and said thin wall tubes covering said contents are adhered to each other at the central part thereof.

5. The endoscope according to claim 4, wherein said thin wall tubes are made of silicone rubber.

6. The endoscope according to claim 5, wherein said thin wall tubes have a length of 20–50 mm and a thickness of 0.1 mm.

7. The endoscope according to claim 4, wherein said thin wall tubes have a length of 20–50 mm and a thickness of 0.1 mm.

* * * * *